United States Patent [19]
Tan et al.

[11] Patent Number: 5,631,361
[45] Date of Patent: May 20, 1997

[54] METHOD OF SYNTHESIZING RADIOISOTOPICALLY LABELED OLIGONUCLEOTIDES BY DIRECT SOLID-PHASE 5' PHOSPHITYLATION

[75] Inventors: Weitian Tan, Framingham; Radhakrishnan P. Iyer, Shrewsbury; Zhiwei Jiang, Grafton; Dong Yu; Sudhir Agrawal, both of Shrewsbury, all of Mass.

[73] Assignee: Hybridon, Inc., Worcester, Mass.

[21] Appl. No.: 447,092

[22] Filed: May 22, 1995

[51] Int. Cl.$^6$ .............................. C07H 1/02; C07H 21/00
[52] U.S. Cl. .............................. 536/25.33; 536/25.3
[58] Field of Search .............................. 536/25.34, 25.33, 536/25.3

[56] References Cited

U.S. PATENT DOCUMENTS

| | | | |
|---|---|---|---|
| 5,047,524 | 9/1991 | Andrus et al. | 536/25.34 |
| 5,281,701 | 1/1994 | Vinayak et al. | 536/25.34 |

OTHER PUBLICATIONS

Cao et al. Tetrahedron Lett. 24(10): 1019–1020, 1983.

*Primary Examiner*—Gary L. Kunz
*Attorney, Agent, or Firm*—Michael S. Greenfield; McDonnell Boehnen Hulbert & Berghoff

[57] ABSTRACT

The present invention comprises a novel method of incorporating radiolabels and other type of labels at one or more predetermined sites within an oligonucleotide. In particular, the method comprises contacting a nascent, support-bound oligonucleotide having an unprotected 5' hydroxyl group with a suitable activating agent, followed by contacting the resulting activated nascent oligonucleotide with a labeled, Y-protected mononucleotide having an unprotected 3'-hydroxyl, thereby condensing the labeled mononucleotide and nascent oligonucleotide. Normal automated synthesis can then be continued to yield the oligonucleotide of desired length having the label in the desired location. This method advantageously yields oligonucleotides with high specific activity. The oligonucleotides thereby produced are useful for determining the pharmacokinetics and biodistribution of their non-radiolabeled counterparts, both in vitro and in vivo.

15 Claims, 3 Drawing Sheets

METHOD OF SYNTHESIZING RADIOISOTOPICALLY LABELED OLIGONUCLEOTIDES BY DIRECT SOLID-PHASE 5' PHOSPHITYLATION

BACKGROUND OF THE INVENTION

1. Field of the Invention

This invention relates to synthetic methods for synthesizing site-specifically radiolabeled oligonucleotides.

2. Summary of the Related Art

Recently, considerable interest has been generated in the development of synthetic oligonucleotides as therapeutic or gene expression modulating agents in the so-called antisense approach. For example, Agrawal, *Trends in Biotechnology* 10, 152–158 (1991), extensively reviews the development of antisense therapeutic approaches. Oligonucleotide phosphorothioates (PS-oligos) have shown great therapeutic potential as antisense-mediated inhibitors of gene expression (Stein and Cheng, *Science* 261, 1004 (1993), and references therein) as evidenced by a number of ongoing clinical trials against AIDS and cancer. Agrawal and Tang, *Antisense Res. and Dev.* 2, 261 (1992), and references therein; and Bayever et at., *Antisense Res. Dev.* 3, 383 (1993).

For an antisense therapeutic approach to be effective, oligonucleotides must be introduced into a patient and must reach the specific tissues to be treated. The biodistribution and pharmacokinetics of a therapeutic drug must be determined as a step preliminary to treatment with the drug. Consequently, there is a need to be able to detect oligonucleotides in body fluids or tissues. Agrawal et al., *Clin. Pharmacokinetics* 28, 7 (1995), reviews certain aspects of the pharmacokinetics of antisense oligonucleotides.

Detection of specific nucleic acid sequences present in cells is generally known in the art. Southern, *J. Mol. Biol.* 98, 503–517 (1975) teaches detection of specific sequences among DNA fragments separated by gel electrophoresis using "blotting" or transfer of the DNA fragments to a membrane followed by hybridization of denatured DNA fragments with a radioactive probe and autoradiography. This procedure has also been extended to the detection of RNA molecules extracted from cells or tissues. E.g., Sambrook et al., *Molecular Cloning: A Laboratory Manual* pp. 7.37–7.52 (Cold Spring Harbor Laboratory Press, 2d Ed. 1989). More recently, faster and quantitative "dot-blotting" procedures have been developed for rapid detection of DNA or RNA from tissues or cells. PCT Application WO 94/16103 discloses a method for detecting the presence of unlabeled synthetic oligonucleotides in body fluids or tissue samples taken from laboratory animal and human patients. In that method, body fluid or tissue samples are taken from an animal or human to whom an oligonucleotide has been administered and are proteolytically digested, then extracted. Total nucleic acids are then transferred to a hybridization membrane. The hybridization membrane with attached nucleic acids is prehybridized, then hybridized with a labeled oligonucleotide that is complementary to the oligonucleotide that was administered to the animal or patient. Presence of hybridized, labeled oligonucleotide is then detected by standard procedures.

Another well-established approach used in in vivo pharmacokinetic studies of pharmacological compounds such as antisense oligonucleotides entails radiolabeling the compounds to enable detection. In animal models, radiolabeled oligonucleotides have been administered to the animal and their distribution within body fluids and tissues has been assessed by extraction of the oligonucleotides followed by autoradiography (See Agrawal et at., *Proc. Natl. Acad. Sci.* 88, 7595–7599 (1991)).

$^{35}$S is a common iostopic label used to study the pharmacokinetics and biodistribution of drug compounds. $^{35}$S-labeling is an established and wide-spread technique. For biological studies, $^{35}$S-labeled oligonucleotide phosphorothioates have been prepared using H-phosphonate chemistry. Garegg et al., *Chem. Scr.* 25, 280–282 (1985). Recently, Iyer et at., *Tel. Lett.* 35, 9521–9524 (1994), disclosed a new compound and methods for synthesizing $^{35}$S site-specifically-labeled oligonucleotide phosphorothioates.

$^{14}$CC and $^{3}$H are two other commonly used isotopic labels. Radioisotopic labeling of synthetic oligonucleotides with $^{14}$C and $^{3}$H is currently accomplished by using the well-established solid-phase automated synthesis. Beaucage and Caruthers, *Tetrahedron Lett.* 22, 1859–1862 (1981); International Application PCT/US85/01148; and Barone et at., *Nucleic Acids Res.* 12, 4051 (1984). In this approach, a 5'-O-DMT-protected mononucleotide is activated at the 3' position by, for example, chloro-(2-cyanoethoxy)-N,N-diisopropylaminophosphine. The resulting 5'-O-DMT-protected 3'-β-cyanoethoxy-N,N-diisopropylamino phosphoramidite mononucleotide is reacted with the unprotected 5'-hydroxyl of an n-mer nascent oligonucleotide, resulting in condensation reaction and the formation of an (n+1)-oligomer.

Cao et at., *Tetrahedron Lett.* 24, 1019 (1983), offered an alternative to this approach. They reported activating the 5'-hydroxyl of the nascent oligonucleotide chain with methyl phosphoroditetrazolide (MPDT) and other heterocyclic bases. Reaction of 5'-DMT-protected mononucleosides having a free 3'-hydroxyl with the activated nascent oligonucleotide resulted in the addition of the mononucleoside to the oligonucleotide by formation of a methyl phosphite triester linkage. Oxidation with iodine in water led to oxidation of the methyl phosphite triester to a methyl phosphonate linkage.

The assembly of $^{14}$C- or $^{3}$H-labeled nucleoside phosphoramidite (3) has generally followed the method of Beaucage and Caruthers and requires a two-step process. (FIG. 1). E.g., Sasmor et al., *J. Labeled Compd. and Radiopharm.* 36, 15–31 (1995). Synthesis is accomplished by addition of the radiolabelled 3'-activated synthon (3) to a unprotected 5'-hydroxyl of a nascent oligonucleotide chain. Several disadvantages are associated with this method: (a) since the radioisotope is introduced in the very first step, the radiochemical yield after two steps is limited; (b) this operation often suffers a dilution problem, namely, the natural abundance isotope is usually blended in as a carrier in order to maintain a manageable synthetic scale, resulting in lower specific activity of the final oligos; (c) the phosphoramidite 3 is a reactive species prone to degradation—3 requires stringent storage and transportation conditions, and the degraded products from 3 could cause insufficient coupling when in use; (d) it is difficult to recover [$^{3}$H]- or [$^{14}$C]-3 intact after the coupling reaction. These drawbacks are costly, considering that in the current coupling protocol 3 and tetrazole are used at more than 10 times excess. Sasmor et al., supra.

Other methods of radiolabeling oligonucleotides, while avoiding the dilution problem, lead to indiscriminate labeling in multiple positions. E.g., Graham et al., *Nucl. Acids Res.* 21, 3737 (1993) and references cited therein. Still other methods employ radiolabeling at exchangeable positions, which magnifies the dilution problem. Graham et al., supra.

In view of the deficiencies in the prior art, improved methods of radiolabeling oligonucleotides are desirable.

3

SUMMARY OF THE INVENTION

The present invention provides new methods for radiolabeling oligonucleotides. In particular, the present invention provides methods for incorporating a radiolabeled nucleoside at one or more predetermined nucleosides within an oligonucleotide. Any suitable radiolabel can be used in the present invention. In a preferred embodiment, the radiolabel is $^{14}C$ or $^{3}H$. The method of the present invention can be used to incorporate other types of labels into oligonucleotides as well.

The present invention provides a method of synthesizing oligonucleotides having a radiolabelled nucleotide at one or more predetermined positions. The method is depicted in FIG. 2 and comprises first activating the 5'-most hydroxyl group of a nascent oligonucleotide by contacting it with a suitable activating agent, such as 2-cyanoethyl N,N, N',N'-tetradiisopropylphosphorodiamidite in $CH_2Cl_2$ in the presence of diisopropylammonium tetrazolide. The activated nascent oligonucleotide is then contacted with a 5'-protected, radiolabelled mononucleotide having an unprotected 3'-hydroxyl, resulting in condensation of the mononucleotide and nascent oligonucleotide.

This method improves upon the prior art methods of incorporating radiolabels into oligonucleotides (as depicted in FIG. 1) in several ways. Because it does not require activating the 5'-protected, radiolabelled mononucleotide 2 (FIG. 1), the present method avoids the loss of radiolabelled mononucleotide due to less than complete, quantitative activation. Accordingly, the present method also avoids the necessity of diluting the radiolabelled mononucleotide with the non-radiolabelled counterpart because of yield loss during the activation process. Consequently, site-specifically radiolabelled oligonucleotides synthesized according to the present method generally have higher specific activity than oligonucleotides produced by prior art techniques. Oligonucleotides synthesized according to the method of the invention have at least about 30% higher specific activity than those synthesized by prior art methods such as described in Sasmor et at., supra. Also, the activated species 3 is reactive and prone to degradation. By activating the nascent oligonucleotide rather than the radiolabelled mononucleotide, the present method eliminates the need of stringent storage and transportation conditions required for the species 3. Furthermore, the present method avoids the difficulty of recovering the reactive radiolabelled species 3 (FIG. 1). The chemically stable radiolabeled mononucleotide 2 is readily recovered after the coupling in the present method by a simple precipitation of tetrazole as tetrazolide. This results in substantial cost savings, because, as previously noted, 3 and tetrazole are used in more than 10 times excess amounts in prior art protocols.

A further advantage of the present method is that the quality of every batch of activated nascent oligonucleotide 6 (FIG. 2) can be easily examined before committing the radiolabeled mononucleotide 2 (FIG. 1) to the coupling reaction. This quality control procedure not only provides a safety precaution but also minimizes the risk of wasting the valuable radioactive precursor.

Oligonucleotides synthesized according to the present method are useful not only for determining the biodistribution of their unlabeled counterparts, but also for determining biostability. Thus, oligonucleotides of the invention are useful to study the pharmacokinetics of therapeutic oligonucleotides in vivo. This is especially useful for determining the site of metabolism of oligonucleotides, which can assist in the design of oligonucleotides having greater biostability.

It can also be useful in delineating the pathway of oligonucleotide metabolism. In addition, radiolabelled oligonucleotides can be used as probes in conventional hybridization assays. Hence, oligonucleotides of the present are useful research tools.

The foregoing merely summarizes certain aspects of the invention and is not intended, nor should it be construed, to limit the invention in any manner. All patents and other documents cited in this specification establish the state of the art and are hereby incorporated by reference in there entirety.

DETAILED DESCRIPTION OF THE PREFERRED EMBODIMENTS

Because of the ever-increasing interest in antisense oligonucleotides as therapeutic agents, there is a need to determine the pharmacokinetics properties of these compounds. It is also necessary to determine biodistribution as well as the half-lives and degradation products of antisense oligonucleotides intended for therapeutic use. One method of accomplishing these tasks is to radiolabel the oligonucleotides. The present method comprises a synthetic technique for radiolabeling oligonucleotides. Any suitable radiolabel can be used in the present invention. In a preferred embodiment, the radiolabel is $^{3}H$ or $^{14}C$, common isotopic labels that allow for tracing and detecting biological compounds, both in vitro and in vivo. The present method is also suitable for incorporating other types of labels in an oligonucleotide, such as fluorescent labels.

In one aspect, the present invention comprises methods of synthesizing oligonucleotides having from one to all radiolabeled nucleotides. The locus or loci of the radiolabels within the oligonucleotide are independent of each other and may be predetermined to be at any position.

Figure 2:
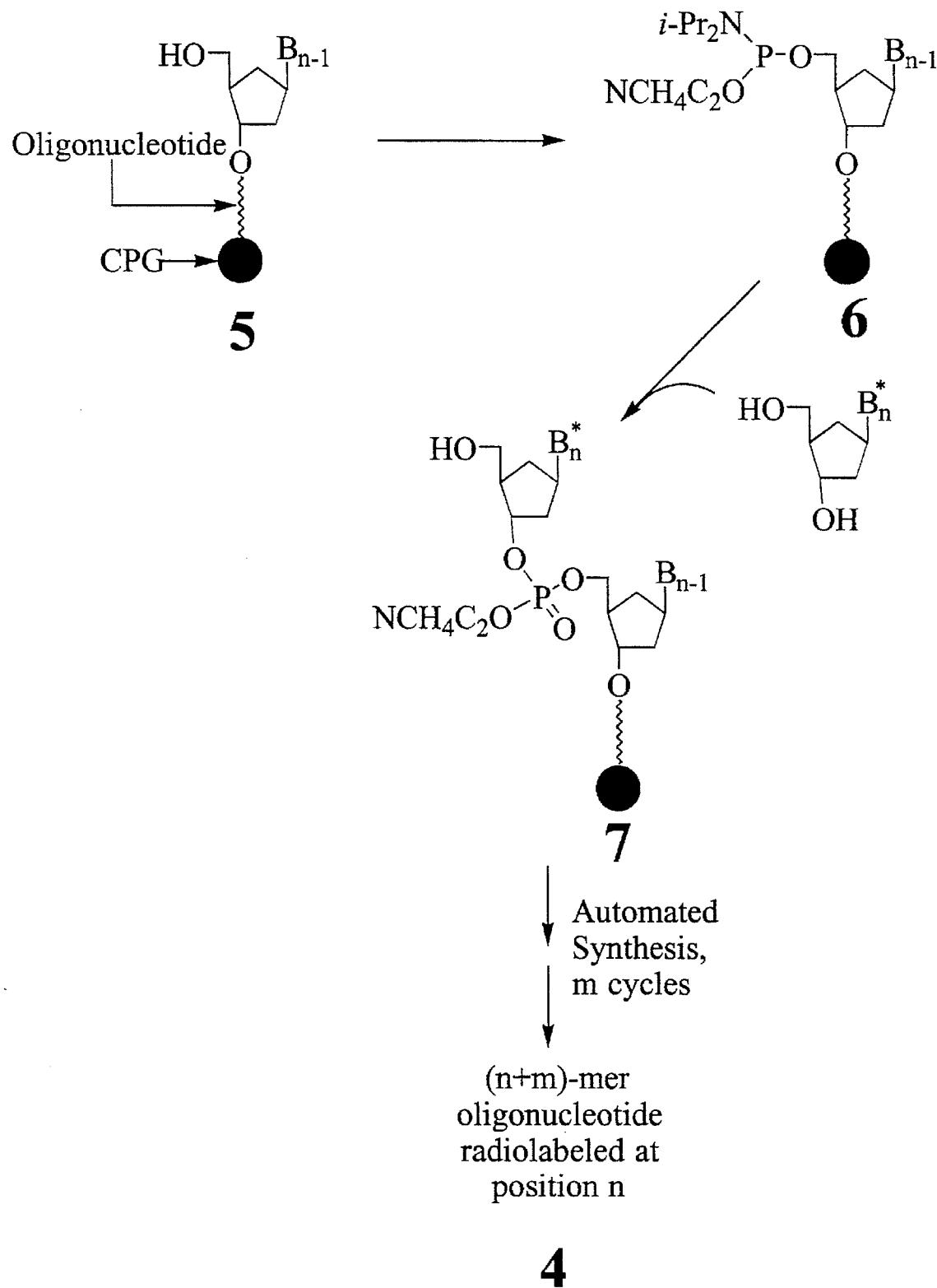
FIG. 2 is a schematic representation of the synthetic method of the present invention. The asterisk indicates a radiolabeled nucleotide.

The present method of synthesizing labeled oligonucleotides comprises contacting a nascent oligonucleotide having an unprotected 5' hydroxyl group with an activating reagent to yield an activated oligonucleotide, and then contacting the activated oligonucleotide with a 5'-protected, labeled mononucleotide having an unprotected 3' hydroxyl. As used herein, the term "nascent oligonucleotide" means a nucleotide chain comprising one or more nucleotides anchored to a solid support. The entire method is conducted in situ and is schematically depicted in FIG. 2.

Any suitable activating agent can be used. Many are known to those skilled in the art. E.g., Beaucage, *Oligodeoxyribonucleotides Synthesis: Phosphoramidite Approach* in *Methods in Molecular Biology*, Vol. 20, *Protocols for Oligonucleotides and Analogs*, pp. 19-(Agrawal, Ed., Humana Press, Totowa, N.J. 1993). In a preferred embodiment, the activating reagent comprises diisopropylammonium tetrazolide and $CH_2Cl_2$ in the presence of 2-cyanoethyl- N,N,N',N'-tetradiisopropylphosphorodiamidite. In this embodiment, the result of activation is the 5'-β-cyanoethyl phosphoramidite 6 depicted in FIG. 2. In another preferred embodiment, 2-cyanoethyl N,N-diisopropylchlorophosphoramidite and diisopropylethylamine in $CH_2Cl_2$ comprise the reagents. Other suitable reagents and activating agents can also be used. See, e.g., Beaucage and Iyer, *Tetrahedron Lett.* 48, 2223 (1982).

The activated nascent oligonucleotide is contacted with a 5'-protected radiolabeled mononucleotide having an unprotected 3'-hydroxyl. This results in coupling of the radiolabeled mononucleotide and the nascent oligonucleotide. Oxidation of the resulting internucleotide linkage yields a β-cyanoethyl phosphate linkage. The method can then be repeated or the nascent oligonucleotide subject to lengthening by any known method. In a preferred embodiment, the 5'-protected mononucleotide is $^{14}C$-labeled at the nucleotide base or $^3H$-labeled at the 5' position.

The reaction conditions of the present invention are not critical. The method may be conducted at room temperature from any where from about 5 minutes to 2 hours. Preferably the reaction is carried out for a time sufficient for the reaction to continue to completion. Generally one hour is sufficient. A number of solvents may be used and are preferrably anhydrous. Such solvents include acetonitrile, N-methyl pyrolidone, dioxane, methylene chloride, and THF. In a preferred embodiment, acetonitrile is used.

The present method may be used to synthesize radiolabeled oligonucleotides having modified or unmodified internucleotide linkages. The modified linkages that can be incorporated consistant with the present invention include, but are not limited to, phosphorothioates, phosphorodithioates, methylphosphonates, and other alkylphosphonates.

Figure 1:
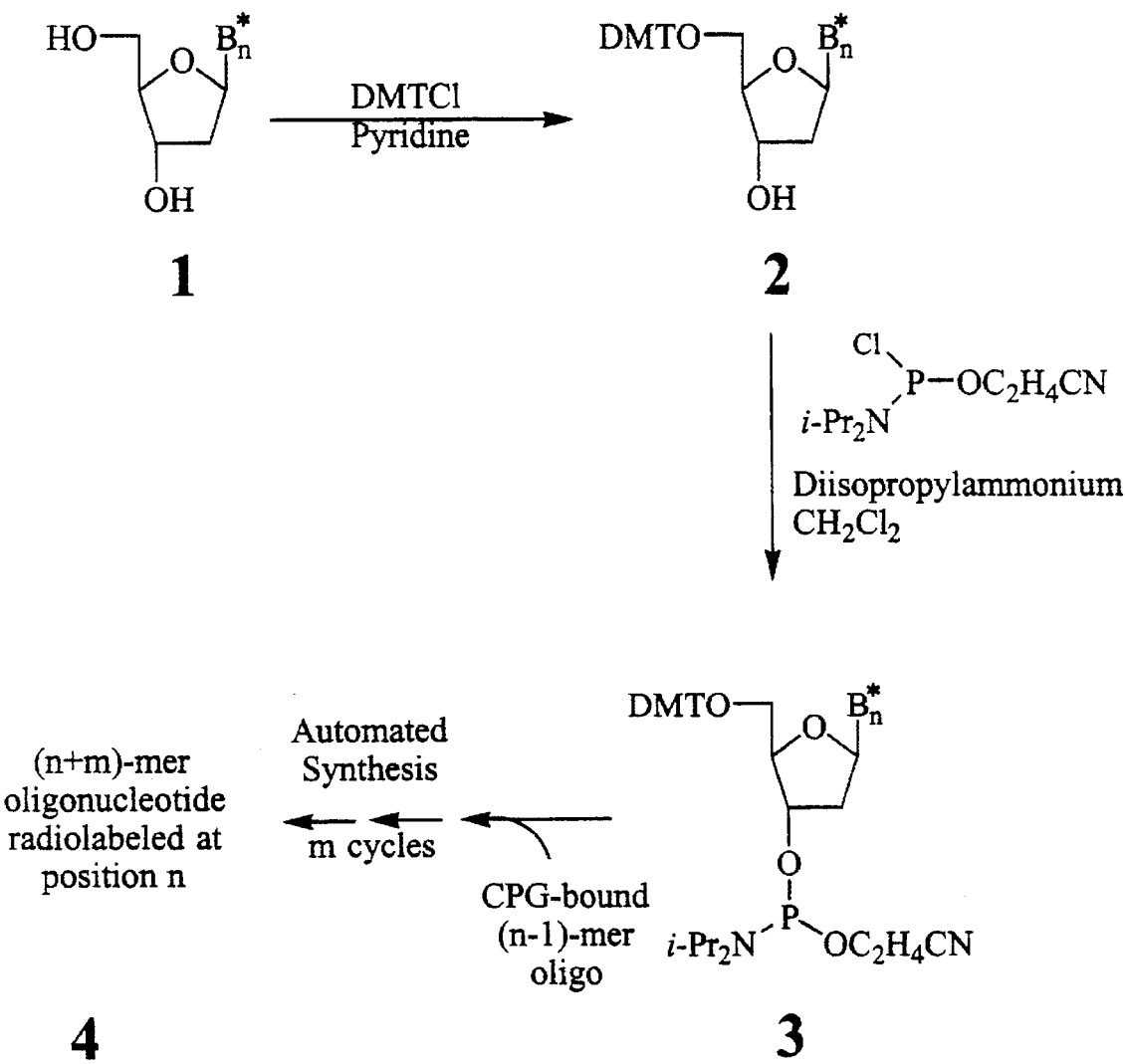
FIG. 1 is a schematic representation of a conventional approach of radiolabeling oligonucleotides.

By comparing FIG. 1 and FIG. 2, some advantages of the present invention are readily appreciated. The present method circumvents the need to isolate and purify the radioactive precursor compounds 3 displayed in FIG. 1. This is beneficial in at least two aspects. The present method avoids the loss due to less than quantitative yield of 3 from 2, and, because 3 is a reactive species prone to degradation, the present method avoids stringent storage and transportation conditions required by 3 and the concomitant loss of 3 due to degradation. Furthermore, oligonucleotides with very high specific activity are more easily obtained using the present method, because, in addition to circumventing the losses described above, the method eliminates the inevitable dilution process in which radioactive precursors are mixed with their natural abundance isotopes to maintain a manageable synthetic scale. Accordingly, the present invention provides a method for synthesizing oligonucleotides with high specific activity having radiolabeled nucleotides at one or more predetermined sites. The specific activity of oligonucleotides synthesized according to the invention can be adjusted downward, of course, by mixing in desired amounts of the non-radiolabeled counterpart.

The present method also provides economic benefits in that whereas it is difficult to recover 3 intact because it is so prone to degradation, the present method allows for simple and efficient recovery of the unreacted radiolabeled precursor 2. This is particularly advantageous when one realizes that in the prior art method 3 is generally used in more than 10 times excess.

Those skilled in the art will appreciate that although the discussion henceforth has focused on radiolabelled oligonucleotides, the method of the present invention is suitably and advantageously used to incorporate a wide variety of modified and untoedified nucleosides into an oligonucleotide. Such modified nucleosides include, but are not limited to, halogenated and flouorescent nucleosides.

The oligonucleotides synthesized by the method of the invention are particularly useful for determining biodistribution and pharmacokinetics of their non-radiolabeled oligonucleotide counterparts. Such methods are well known to those skilled in the art. E.g., Agrawal et at., *Clin. Pharmacokinetics*, supra.

Generally, however, oligonucleotides of the invention are useful for any purpose for which their non-radiolabeled oligonucleotide counterparts are useful. For example, oligonucleotides of the invention are valuable for studying the role of a targeted gene in biological processes, because the oligonucleotides are useful tools for easily and selectively inhibiting expression of the targeted nucleic acid. The oligonucleotides of the present invention provide an alternative to the laborious method of gene mutation to inhibit expression and study the effect of loss of such expression. The importance of such an alternative is easily appreciated when one realizes that the elucidation of most known biochemical processes has been done by deletion mutation.

The following Examples are offered for illustrative purposes only and are not intended, nor should they be construed, as limiting the invention in any manner.

EXAMPLES

EXAMPLE 1

Synthesis of C $^{14C}$TCC

Figure 3:
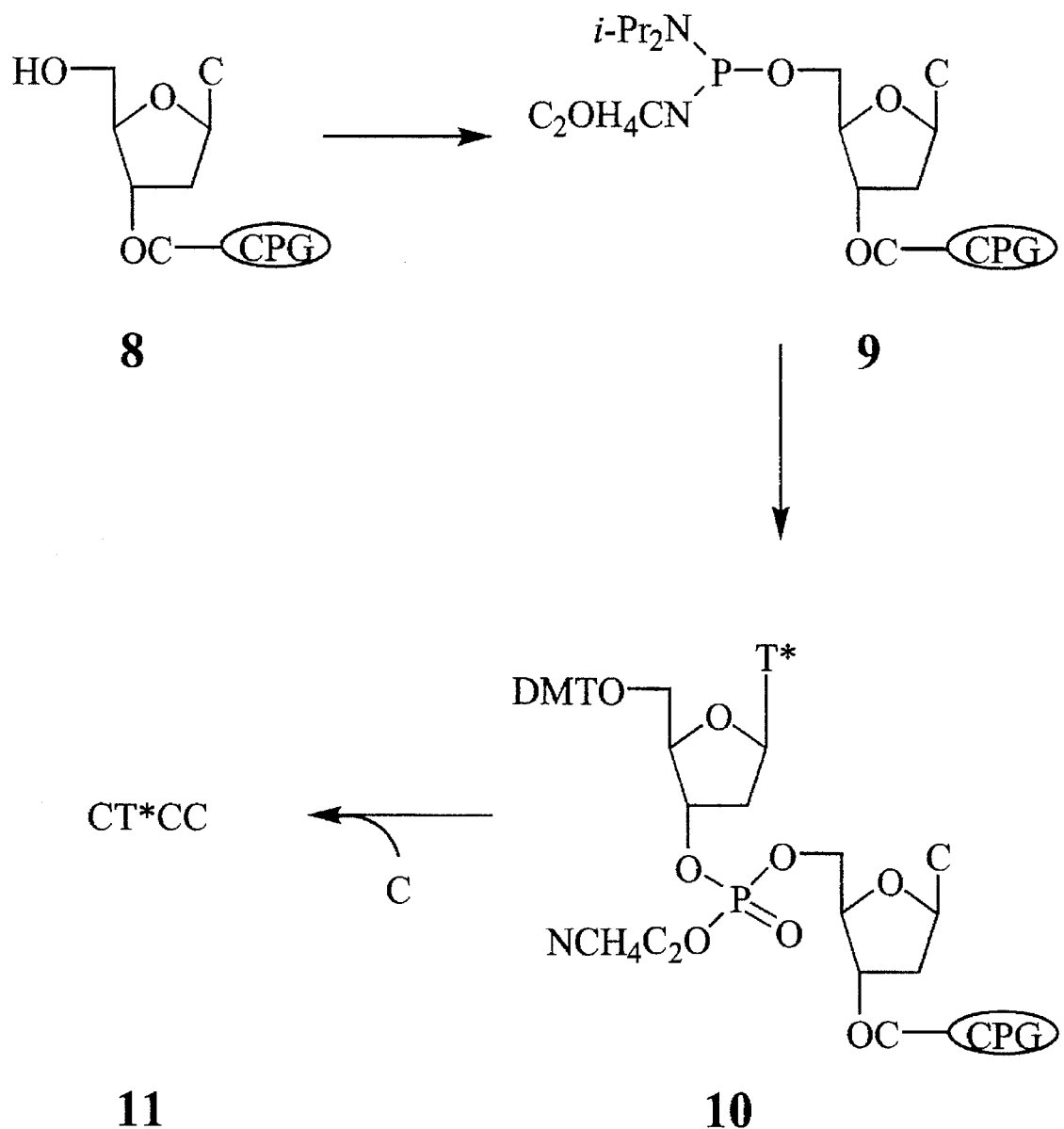
FIG. 3 is a schematic representation of the chemical synthesis of the radiolabeled tetramer SEQ ID NO 1. The asterisk indicates a radiolabeled nucleotide.

The trityl-off dimer CC (8 in FIG. 3) was synthesized at 2×1 µmol scale using phosphoramidite chemistry in an automated DNA synthesizer (Expedite 8909, Biosearch, Milford, Mass.). The vacuum-dried dimer 8 was placed in an eppendorf tube (1.5 ml) and treated with a solution of 2-cyanoethyl N,N,N',N'-tetradiisopropylphosphorodiamidite (200 µl, 0.15M in $CH_3CN$) in the presence of diisopropylammonium tetrazolide (2.57 mg, 15 µmol) at 25° C. for 1 hour. Unless stated otherwise, all chemicals were obtained from Aldrich (Milwaukee, Wis.). The resultant CPG phosphoramidite 9 (FIG. 3) was washed with $CH_2Cl_2$ (10×1 ml) and dried in vacuo.

The quality of a CPG-bound nucleoside phosphoramidite 9 was examined by treating 0.5 µmol of it with DMT-thymidine (50 µl, 0.1M in THF) and tetrazole (30 µl, 0.45M in $CH_3CN$) at 25° C. for 1 hour. After oxidation with 0.1M $I_2$ in THF/py/$H_2O$ (90/5/5) for 2 Min, the CPG material 10 (FIG. 1) was treated with $Cl_2CHCO_2H$ (3% in $CH_2Cl_2$) at 25° C. for 5 min. The resultant DMT-cation was subject to a trityl assay performed according to standard procedures. Although phosphitylation and coupling yields were not optimized, about 80–95% of the CC dimer 8 was found to be coupled. Phosphitylation with 2-cyanoethyl N,N-diisopropylchlorophosphoramidite and diisopropylethylamine in $CH_2Cl_2$ achieved similar results.

After quality examination, the amidite 9 (1.5 µmol) was treated with a mixture of 5'-O-dimethoxytrityl-[2-$^{14}C$]-thymidine (75 µL, 0.2M in anhydrous THF) and 60 µL of 0.45 M tetrazole (30 min, 25° C.). Oxidation with 0.1M $I_2$ in THF/py/$H_2O$ (90/5/5) for 1 min afforded [2-$^{14}C$]10 (FIG. 3), which was immediately washed with $CH_3CN$ (10×1 ml). Subsequently, [2-$^{14}C$]10 was used as a "T" column to automate a standard "C" cycle synthesis to furnish the CPG-bound [2-$^{14}C$]11 (FIG. 3), which was treated with $NH_4OH$ (28%, 3 ml, 55° C., 16 h). Evaporation with a Speed-Vac gave the crude [2-$^{14}C$]11 as a light-yellow pellet. PAGE purification (20%, 7M urea) provided [2-$^{14}C$]11 as a white pellet (11 $AU_{260}$, 14.8 µCi, 53 µCi/µmol). PAGE and HPLC analyses demonstrated that $C^{14c}TCC$ was identical to the authentic tetramer CTCC synthesized according to standard techniques. All HPLC analyses were done with MILLENNIUM software on a Waters 600 Controller with a 996 Photodiode Array UV detector (200–320 nm) interfaced with a Packard Radiomatic 525 TR Flow Scintillation Analyzer (0–156 Kev, $^{14}C$ flow-counting efficiency at about 95%). Scintillation cocktail (ULTIMA-FLOW AP) was auto-mixed with HPLC flow-buffer at 3:1 ratio after UV detection and pumped into a scintillation flow-cell (500 µl) in about 40 sec delay time.

EXAMPLE 2

Synthesis of $C^{14c}TCC$ Having Modified Internucleotide Linkages

The tetramer $C^{14c}TCC$ was synthesized according to the method of Example 1, once incorporating phosphorothioate internucleotide linkages and once incorporating methyl phosphonate linkages using standard procedure. *Methods in Molecular Biology*, Vol. 20, *supra*, pp. 143–189. Comparisons using HPLC with UV detection interfaced with radiometric flow detection demonstrated that in each instance the tetramer labeled according to the method of the invention was identical to its unlabeled counterpart synthesized using standard techniques.

EXAMPLE 3

Enzymatic Digestion of $C^{14c}TCC$

A purified sample of the radiolabeled tetramer 11 was synthesized as described in Example 1. The amidite 9 (1 µmol) was treated at 25° C. with a mixture of 2 (0.2M in THF) and tetrazole (0.45M in $CH_3CN$) for 30 min. The liquid was collected and the CPG material was rinsed with $CH_3CN$. The liquid and the rinse were combined for later use in recovery of unreacted 2. Example 4, infra. The tetramer 11 was digested first with *Snake Venom Phosphodiesterase* and then with *Bacterial Alkaline Phosphatase*. Each enzymatic digestion was allowed to run at 37° C. for 1 day using standard conditions and procedures. The digested samples were analyzed by reverse-phase HPLC, monitored simultaneously by UV and flow-radioactive detectors. Reverse-phase HPLC was carried out using a NOVA-PAK $C_{18}$column (3.9×150 mm) at 25° C. with isocratic mobile phase ($H_2O$/2M TEAA/$CH_3$ CN, 92:5:3, v/v/v, flow rate 0.5 ml/min) over 30 min. The peak index plot was programmed by recording the UV spectra (240–300 nm) at each peak apex of the chromatogram ($\lambda_{260}$). The two detected peaks (rentention times of 3.38 and 7.38 min.) match standard dC and T, respectively. The HPLC profiles showed that only the thymidine peak carried the $^{14}C$ label.

EXAMPLE 4

Recovery of Unreacted Radiolabeled 5'-Protected Mononucleotide

To demonstrate that the present method is economically efficient because it advantageously allows for recovery of radiolabeled reactants, we recovered the unreacted radiolabeled mononucleotide 2 by addition of 100 µl of diisopropylamine into the combined liquid and rinse collected in Example 3. The salt was collected (99% recovery). Repeated evaporation of the supernatant to remove the excessive amine with $CH_3CN$ provided a white crystalline solid.

Radio-HPLC analysis (normal phase with silica packing) using an isocratic mobile phase ($CH_2Cl_2$/$CH_3OH$/TEA, 95/4.5/0.5, flow rate: 1.5 ml/min) revealed that the recovered radioactive compound was pure 2 ($\lambda_{max}$=238.4 nm; retention time=19.7 min.). The total recovery efficiency was about 92%.

We claim:

1. A method of synthesizing labeled oligonucleotides comprising contacting a nascent oligonucleotide having an unprotected 5' hydroxyl group with an activating reagent to yield an activated oligonucleotide, and then contacting the activated oligonucleotide with a 5'-protected, labeled mononucleotide having an unprotected 3' hydroxyl, wherein the activated oligonucleotide is a phosphoramidite.

2. The method according to claim 1, wherein the activating reagent comprises diisopropylammonium tetrazolide, $CH_2Cl_2$, and 2-cyanoethyl-N,N,N',N'-tetradiisopropylphosphorodiamidite.

3. The method according to claim 1, wherein the activating reagent comprises 2-cyanoethyl N,N-diisopropylchlorophosphoramidite and diisopropylethylamine in $CH_2Cl_2$.

4. A method according to claim 1, wherein the label is a radiolabel.

5. The method according to claim 4, wherein the activating reagent comprises diisopropylammonium tetrazolide, $CH_2Cl_2$, and 2-cyanoethyl-N,N,N',N'-tetradiisopropylphosphorodiamidite.

6. The method according to claim 4, wherein the activating reagent comprises 2-cyanoethyl N,N-diisopropylchlorophosphoramidite and diisopropylethylamine in $CH_2Cl_2$.

7. A method according to claim 4, wherein the radiolabel is $^{14}C$.

8. The method according to claim 7, wherein the activating reagent comprises diisopropylammonium tetrazolide, $CH_2Cl_2$, and 2-cyanoethyl-N,N,N',N'-tetradiisopropylphosphorodiamidite.

9. The method according to claim 7, wherein the activating reagent comprises 2-cyanoethyl N,N-diisopropylchlorophosphoramidite and diisopropylethylamine in $CH_2Cl_2$.

10. A method according to claim 4, wherein the radiolabel is $^3H$.

11. The method according to claim 10, wherein the activating reagent comprises diisopropylammonium tetrazolide, $CH_2Cl_2$, and 2-cyanoethyl-N,N,N',N'-tetradiisopropylphosphorodiamidite.

12. The method according to claim 10, wherein the activating reagent comprises 2-cyanoethyl N,N-diisopropylchlorophosphoramidite and diisopropylethylamine in $CH_2Cl_2$.

13. A method according to claim 1, wherein the label is fluorescent.

14. The method according to claim 13, wherein the activating reagent comprises diisopropylammonium tetrazolide, $CH_2Cl_2$, and 2-cyanoethyl-N,N,N',N'-tetradiisopropylphosphorodiamidite.

15. The method according to claim 13, wherein the activating reagent comprises 2-cyanoethyl N,N-diisopropylchlorophosphoramidite and diisopropylethylamine in $CH_2Cl_2$.

* * * * *